United States Patent
Strandborg et al.

(10) Patent No.: US 12,197,645 B1
(45) Date of Patent: Jan. 14, 2025

(54) SYSTEM AND METHOD OF REMOTE RENDERING BASED ON VESTIBULO-OCULAR REFLEX MOVEMENT

(71) Applicant: Varjo Technologies Oy, Helsinki (FI)

(72) Inventors: Mikko Strandborg, Hangonkylä (FI); Mikko Ollila, Tampere (FI)

(73) Assignee: Varjo Technologies Oy, Helsinki (FI)

( * ) Notice: Subject to any disclaimer, the term of this patent is extended or adjusted under 35 U.S.C. 154(b) by 0 days.

(21) Appl. No.: 18/513,717

(22) Filed: Nov. 20, 2023

(51) Int. Cl.
  G06F 3/01 (2006.01)
  A61B 3/113 (2006.01)
  A61B 5/16 (2006.01)
  G02B 27/00 (2006.01)

(52) U.S. Cl.
  CPC .............. G06F 3/013 (2013.01); G06F 3/012 (2013.01); *A61B 3/113* (2013.01); *A61B 5/163* (2017.08); *G02B 27/0093* (2013.01)

(58) Field of Classification Search
  CPC ......... G06F 3/013; G06F 3/012; A61B 3/113; A61B 5/6821; A61B 5/163; A61B 3/0091; G02B 27/0093; G02B 2027/0187; G16H 40/67
  See application file for complete search history.

(56) References Cited

U.S. PATENT DOCUMENTS

| | | | |
|---|---|---|---|
| 9,517,008 B1* | 12/2016 | Berme | A61B 8/10 |
| 10,018,847 B2* | 7/2018 | Li | G06F 3/012 |
| 10,136,810 B2* | 11/2018 | Migliaccio | A61B 3/113 |
| 10,231,614 B2* | 3/2019 | Krueger | A61B 5/11 |
| 11,389,059 B2* | 7/2022 | Krueger | A61B 5/163 |
| 2020/0305707 A1* | 10/2020 | Fink | A61B 3/0025 |
| 2022/0070567 A1* | 3/2022 | Skoglund | G06F 3/013 |
| 2024/0108275 A1* | 4/2024 | Shindo | A61B 10/00 |

* cited by examiner

*Primary Examiner* — Rodney Amadiz
(74) *Attorney, Agent, or Firm* — Ziegler IP Law Group LLC.

(57) ABSTRACT

Disclosed is a system with at least one server that is communicably coupled to at least one display apparatus, wherein the at least one server is configured to detect a start of a Vestibulo-Ocular Reflex (VOR) movement (T1) based on a gaze tracking-data and a pose tracking-data received from the at least one display apparatus; control remote rendering of an extended reality video stream at the at least one display apparatus by modifying a head pose data indicated in the pose tracking-data and a gaze direction data indicated in the gaze tracking-data such that a total retinal angular velocity of a focus target approaches a zero value during a VOR movement (T2); detect an end of the VOR movement (T3); and stop the modification and revert video rendering parameters to pre-set default settings after the end of the VOR movement (T3).

15 Claims, 2 Drawing Sheets

SYSTEM AND METHOD OF REMOTE RENDERING BASED ON VESTIBULO-OCULAR REFLEX MOVEMENT

TECHNICAL FIELD

The present disclosure relates to systems for remote rendering. The present disclosure also relates to methods of remote rendering based on Vestibulo-Ocular Reflex (VOR) movement.

BACKGROUND

In recent times, the field of extended reality (XR) technology has witnessed substantial growth and adoption over the years. Currently, immersive extended-reality (XR) technologies are employed in various fields, such as entertainment, real estate, training, medical imaging, simulators, navigation, and the like. Such immersive XR technologies create XR environments for presentation to users of XR devices (such as an XR headset, pairs of XR glasses, or other devices).

However, existing systems and techniques for generating images have several problems associated therewith. For example, the existing systems and techniques are typically inefficient in adapting to the dynamic nature of human vision during head and eye movements. The existing systems and techniques fail to maintain visual clarity, stability, and comfort for users, particularly during head and eye movements, leading to reduced image quality and motion-induced discomfort, hindering the immersive experience. In addition, the existing systems and techniques struggle to adapt to users' visual acuity and perception, limiting the realistic experience, XR can offer.

Therefore, in light of the foregoing discussion, there exists a need to overcome the aforementioned drawbacks.

SUMMARY

The aim of the present disclosure is to provide a system and a method of remote rendering with an improved visual quality of extended reality (XR) transport during the time the eyes are in Vestibulo-Ocular Reflex (VOR) movement. The aim of the present disclosure is achieved by a system and a method of remote rendering based on the VOR movement for enhancing the visual quality and comfort of XR experiences by dynamically adjusting the video rendering parameters during the VOR movement, prioritizing the visual clarity during the head movement of the user, as defined in the appended independent claims to which reference is made. Advantageous features are set out in the appended dependent claims.

Throughout the description and claims of this specification, the words "comprise", "include", "have", and "contain" and variations of these words, for example, "comprising" and "comprises", mean "including but not limited to", and do not exclude other components, items, integers, or steps not explicitly disclosed also to be present. Moreover, the singular encompasses the plural unless the context otherwise requires. In particular, where the indefinite article is used, the specification is to be understood as contemplating plurality as well as singularity, unless the context requires otherwise.

DETAILED DESCRIPTION OF EMBODIMENTS

Figure 1:
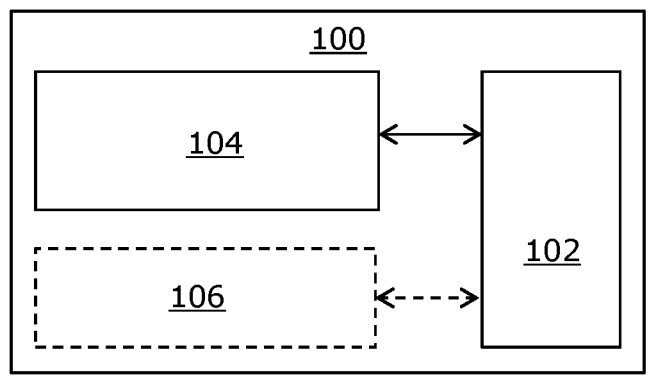
FIG. 1 is an illustration of a block diagram of an architecture of a system of remote rendering based on Vestibulo-Ocular Reflex (VOR) movement, in accordance with an embodiment of the present disclosure.

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In a first aspect, an embodiment of the present disclosure provides a system comprising at least one server that is communicably coupled to at least one display apparatus, wherein the at least one server is configured to:
  detect a start of a Vestibulo-Ocular Reflex (VOR) movement (T1) based on a gaze tracking-data and a pose tracking-data received from the at least one display apparatus;
  control remote rendering of an extended reality video stream at the at least one display apparatus by modifying a head pose data indicated in the pose tracking-data and a gaze direction data indicated in the gaze tracking-data such that a total retinal angular velocity of a focus target approaches a zero value during a VOR movement (T2);
  detect an end of the VOR movement (T3); and
  stop the modification and revert video rendering parameters to pre-set default settings after the end of the VOR movement (T3).

In a second aspect, an embodiment of the present disclosure provides a method of remote rendering implemented by at least one server, the method comprising:
  detecting a start of a Vestibulo-Ocular Reflex (VOR) movement (T1) based on a gaze tracking-data and a pose tracking-data received from the at least one display apparatus;
  controlling remote rendering of an extended reality video stream at the at least one display apparatus by modifying a head pose data indicated in the pose tracking-data and a gaze direction data indicated in the gaze tracking-data such that a total retinal angular velocity of a focus target approaches a zero value during the VOR movement (T2);
  detecting an end of the VOR movement (T3); and
  ending the modification and reverting video rendering parameters to pre-set default settings after the end of the VOR movement (T3).

The present disclosure provides the aforementioned system and the aforementioned method, for enhancing the quality of extended reality (XR) experiences during VOR movements. The detection of the start of a VOR movement (T1) is utilized to control the remote rendering by modifying the head pose data indicated in the pose tracking-data and the gaze direction data, resulting in an improved clear visual during the head movement at the display apparatus. Moreover, by keeping the total retinal angular velocity close to zero during VOR movements, the system ensures that the perceived visual experience remains stable and comfortable, reducing motion sickness and improving the overall quality of extended reality content. Furthermore, the detection of the end of the VOR movement (T3) and return of the video rendering parameters to pre-set default settings ensures a seamless transition with a comfortable and uninterrupted XR experience. As a result, the real-time adaptation and sensory continuity facilitated by the aforementioned system and the aforementioned method provide a highly immersive XR experience that responds to the user's gaze and VOR movement. This, in turn, leads to a significant enhancement in the overall quality of the extended reality encounter.

Throughout the present disclosure, the term "at least one display apparatus" refers to specialized equipment that is capable of at least displaying a video stream. The video stream is to be presented to a user of the at least one display apparatus. It will be appreciated that the term "at least one display apparatus" encompasses a head-mounted display (HMD) device and, optionally, a computing device communicably coupled to the HMD device. The term "head-mounted display" device refers to specialized equipment that is configured to present an extended-reality (XR) environment to a user when said HMD device, in operation, is worn by said user on his/her head. The HMD device is implemented, for example, as an XR headset, a pair of XR glasses, and the like, that is operable to display a visual scene of the XR environment to the user. Examples of the computing devices include, but are not limited to, a laptop, a desktop, a tablet, a phablet, a personal digital assistant, a workstation, and a console. The term "extended-reality" encompasses virtual reality (VR), augmented reality (AR), mixed reality (MR), and the like. The at least one server could be remotely located from the at least one display apparatus. Optionally, upon foveating the video stream, the at least one server is configured to send the (foveated) video stream to the at least one display apparatus for displaying thereat.

Notably, the at least one server controls the overall operation of the system. The at least one server is communicably coupled to (a processor of) the at least one display apparatus, for example, via a communication network.

Throughout the present disclosure, the term "Vestibulo-Ocular Reflex (VOR) movement" refers to a reflex acting to stabilize gaze during head movement, with eye movement due to activation of the vestibular system. The reflex acts to stabilize images on the retinas of the eye during head movement. Moreover, the gaze is held steadily on a location by producing eye movements in the direction opposite that of head movement. For example, when the head moves to the right, the eyes move to the left, meaning the image a person sees stays the same even though the head has turned. Since slight head movement is present all the time, VOR is necessary for stabilizing vision. Processing the gaze tracking-data and the pose tracking-data to detect the start of the VOR movement (T1) and the end of the VOR movement (T3) is well-known in the art. The technical effect of detecting the start of the VOR movement (T1) and the end of the VOR movement (T3) is to allow the system to proactively respond to the user's visual intent, leading to a superior, distraction-free user experience when a user's head is in motion. In addition, the detection of the start of the VOR movement (T1) is used to ensure that the visuals remain stable and in focus to further enhance the overall responsiveness and overall user XR experience. Furthermore, the detection of the end of the VOR movement (T3) is used to restore the video rendering parameters to their original values.

The term "gaze tracking data" refers to data that includes images/videos of the user's eye, sensor values, and the like that are received from the at least one display apparatus. Optionally, the at least one display apparatus is configured to employ at least one of: an image processing algorithm, a feature extraction algorithm, or a data processing algorithm. Techniques and algorithms for processing the gaze-tracking data to determine the gaze direction are well-known in the art. It will be appreciated that the gaze-tracking data is collected repeatedly throughout a given session of using the at least one display apparatus, as the gaze of the user's eye keeps changing whilst the at least one display apparatus is in use. It will also be appreciated that the aforesaid information is obtained by the at least one processor in real-time or near-real time.

Throughout the present disclosure, the term "pose-tracking data" refers to information related to the position and orientation of the image sensor or camera in a real-world environment of the at least one display apparatus. The pose-tracking data is collected by the pose-tracking means. In this regard, the term "pose-tracking means" refers to specialized equipment that is employed to detect and/or follow the pose (namely, a position and orientation) of the image sensor within the real-world environment. In practice, the aforesaid pose-tracking means is employed to track a pose of the image sensor. Pursuant to embodiments of the present disclosure, the aforesaid pose-tracking means is implemented as a true SixDegrees of Freedom (6DoF) tracking system. In other words, said means track both the position and the orientation of the at least one camera within a three-dimensional (3D) space of the real-world environment, which is represented by the aforementioned global coordinate system. In particular, said pose-tracking means configured to track translational movements (namely, surge, heave, and sway movements) and rotational movements (namely, roll, pitch, and yaw movements) of the at least one camera within the 3D space. Moreover, the term the term "pose" refers to both position and orientation. Thus, the pose of the image sensor comprises the 3D position and 3D orientation of the image sensor within the aforementioned 3D space of the real-world environment.

The pose-tracking data is processed to determine the corresponding poses of the image sensor with respect to which said images of said sequence are captured. In order to determine the corresponding pose of the image sensor at a sub-pixel accuracy, the pose-tracking means may be implemented as multiple tracking means. The pose-tracking means may be implemented as the multiple-tracking means for determining the corresponding pose of the image sensor accurately. The pose-tracking means may be implemented as the multiple tracking means by systems including but not limited to, an optics-based tracking system (inside-out and/or outside-in), a magnetism-based tracking system, an accelerometer, a gyroscope, an Inertial Measurement Unit (IMU), a Timing and Inertial Measurement Unit (TIMU). The accuracy of the pose could be improved by correlating the pose-tracking data of the multiple tracking means. The determination of the pose is used to provide a better tracking quality as a frame of reference for adjusting another pose corresponding to a lower tracking quality ensuring improvement in the accuracy of the other pose upon adjustment, whilst also ensuring that the accuracy of the given pose is not compromised in making the said adjustment. The imaging system's ability to determine the exact pose of the camera with subpixel accuracy ensures that the images are correctly aligned and calibrated, reducing distortions and artifacts.

Optionally, the at least one server is further configured to utilize a combination of the gaze-tracking data and the pose-tracking data as an additional datapoint during the VOR movement (T2) to refine tracking of at least one or both of the head pose and the gaze-direction.

In this regard, the term "additional datapoint" refers to data that is received from the at least one display apparatus and is used to refine the tracking of at least one or both of the head poses and the gaze direction accurately and precisely. For example, when the user wearing an XR headset turns his/her head to explore a virtual environment during VOR movements, the at least one server is configured to utilize both gaze-tracking data (eye movement) and pose-tracking data (head movement) data to ensure that the XR system accurately follows the user's head orientation and gaze direction. As a result, the technical effect of utilizing a combination of the gaze-tracking data and the pose-tracking data as an additional datapoint during the VOR movement (T2) to refine tracking of at least one or both of the head pose, and the gaze-direction is to optimize tracking of the user's head pose and gaze direction for an enhanced user XR experience.

Throughout the present disclosure, the term "remote rendering" refers to the process of generating and rendering visual content, such as images, XR video streams, and the like. The at least one server is configured to control the remote rendering of an extended reality video stream at the at least one display apparatus such that a total retinal angular velocity of a focus target approaches a zero value during a VOR movement (T2). In this regard, the term "total retinal angular velocity" refers to an angular velocity as the rate at which an image moves across the retina during eye or head movements. For example, if the user is tracking an object in motion relative to the user's head, then, in that case, the angular velocity of the object relative to the user's head is non-zero, but due to the compensatory tracking motion of the user's eyes to follow the target the total retinal angular velocity of the object approaches zero. The total retinal angular velocity allows the system to precisely adapt the rendering of content in response to the user's eye and head movements. By keeping the total retinal angular velocity close to zero during VOR movements, the system ensures that the perceived visual experience remains stable and comfortable, reducing motion sickness and improving the overall quality of extended reality content.

Throughout the present disclosure, the term "video rendering parameters" refers to the parameters that are used to display the video content on the at least one display apparatus, such as resolution, frame rate, compression, and other visual characteristics. Moreover, when the VOR movement (T3) ends, the video rendering parameters are further reverted to the pre-set default settings. In this regard, the term "pre-set default settings" refers to standard or predetermined values for video rendering parameters that are established as the baseline or starting point. The technical effect of controlling the remote rendering of an extended reality video stream is to adjust the rendering of the XR content to match the natural movement of the user's eyes and head. As a result, the system is configured to allow an enhanced immersive, and comfortable extended reality experience by minimizing any discrepancies between the user's perception and the rendered content.

Optionally, the control of the remote rendering of the extended reality video stream comprises:
tracking an object in motion in the field of view of an image sensor of the at least one display apparatus; and
detecting and differentiating between a movement of the tracked object in motion from a point of view of the image sensor with respect to a stationary perception of the object in motion from a user's eye perspective during the VOR movement (T2).

Throughout the present disclosure, the term "object in motion" refers to a computer-generated or real-world object (namely, a digital object) or an image region in motion in a field of view. Examples of the object in motion may include, but are not limited to, a wide range of objects, such as physical objects, virtual objects in the XR environment, or moving elements within a video or image, such as a virtual navigation tool (such as a virtual map, a virtual direction signage, and so forth), a virtual gadget (such as a virtual calculator, a virtual computer, and so forth), a virtual message (such as a virtual instant message, a virtual chat conversation, a virtual to-do note, and so forth), a virtual entity (such as a virtual person, a virtual animal, a virtual ghost, and so forth), a virtual entertainment media (such as a virtual painting, a virtual video, a virtual interactive advertisement, and so forth), a virtual vehicle or part thereof (such as a virtual car, a virtual cockpit, and so forth), and virtual information (such as a virtual news description, a virtual announcement, virtual data, and so forth). Moreover, it will be appreciated to note that when the human eye is in smooth pursuit movement (tracking a moving object), then, in that case, the visual acuity of the rest of the field of view is diminished due to motion blur. Hence, the detection of the object in motion accurately becomes more challenging. In this regard, the term "field of view" captured by the image sensor of the at least one display apparatus refers to an observable extent of the real-world environment that is captured by the image sensor. The field of view of the image sensor is expressed in terms of degrees or radians. The field of view of the image sensor may depend on the size of the image sensor. Optionally, the field of view of the image sensor is greater than 150 degrees. As an example, the field of view of the image sensor may be 150, 160, 170, 180, 190, 200, 210, 220 degrees, and so forth. In this regard, the term "image sensor" refers to a device that detects light from the real-world environment at its photo-sensitive surface when said light is incident thereupon. The image sensor comprises a plurality of photo-sensitive elements, which collectively form the photo-sensitive surface of the image sensor. Upon such detection of the light from the real-world environment, the plurality of photo-sensitive elements captures a plurality of image signals. The plurality of image signals are electrical signals pertaining to a real-world scene of the real-world environment. The plurality of image signals are processed (by an image signal processor or the processor of the imaging apparatus) to generate a digital image. A given photo-sensitive element is known as a picture element or a pixel. It will be appreciated that the plurality of photo-sensitive elements could be arranged in a required manner (for example, such as a rectangular two-dimensional (2D) grid, a polygonal arrangement, a circular arrangement, an elliptical arrangement, a freeform arrangement, and the like) to form the photo-sensitive surface of the image sensor. Examples of the image sensor include, but are not limited to, a charge-coupled device (CCD) image sensor and a complementary metal-oxide-semiconductor (CMOS) image sensor. The technical effect of detecting objects in motion within the field of view captured by an image sensor is to enhance user interaction and user experience, particularly in extended reality (XR) applications, enabling realistic object tracking and reducing user effort. The technical effect of detecting and differentiating between the movement of the tracked object in motion from the point of view of the image sensor is to provide enhanced visual clarity of the object in motion and to create a realistic and comfortable user perception during VOR movements for an enhanced immersive XR experience.

Optionally, the control of the remote rendering of the extended reality video stream further comprises executing a video see-through (VST) adjustment to balance between deblur and sharpening parameters, based on the differentiation during the VOR movement (T2).

Herein, the term "video see-through (VST) adjustment" refers to a technique that is used in augmented reality (AR) and mixed reality (MR) display apparatus(es) to provide real-time modification of visual content to create a seamless blend between the real world (captured by a camera) and virtual elements. Examples of the VST adjustment may include, but are not limited to the adjustment of brightness, color, transparency, size of virtual objects, and the like to make them appear more realistic and consistent with the real-world surroundings. Moreover, the term "deblur and sharpening parameters" refers to settings or configurations that control the level of blurriness or sharpness in visual content and can be used to determine how much image smoothing or sharpening should be applied to the displayed content. These settings aim to improve the clarity of visual elements and enable the users to view the objects more distinctly and clearly with fine details or edges. In an implementation, the sharpening parameters are adjusted by kernel size, kernel values, kernel types, and gain of unsharp mask that enables the at least one server to accommodate the fact that even though the tracked object is moving from the camera sensor's perspective, it's not moving from the eye's perspective, so change deblur/sharpening settings accordingly. The technical effect of executing a video see-through (VST) adjustment based on the detected differentiation during VOR movement (T2), is to optimize the balance between deblur and sharpening parameters for objects in motion. As a result, such adjustment is used to ensure that moving objects are rendered with optimal visual clarity, aligning with the user's natural perception during smooth pursuit, and creating a more realistic XR experience.

Optionally, the at least one server is further configured to control switching of a lock mode at the at least one display apparatus to lock a head pose indicated in the pose tracking data and the gaze direction indicated in the gaze tracking data during the VOR movement (T2).

Herein, the term "control switching of a lock mode" corresponds to the managing of the activation and deactivation of a lock mode in the system. For example, when a user is engaged in head movements (VOR movement), then, in that case, the at least one server is configured to activate a lock mode that holds the user's head and gaze direction steady, enhancing the user's ability to focus on specific objects or elements in the XR environment. In an implementation, the lock mode is applied to the combination of head movement and the gaze movement of the user in order to synchronize the gaze tracking data and pose tracking data such that the world-space gaze direction (i.e., the sum of head orientation and the gaze orientation) is constant. In another implementation, the lock mode is applied when the total retinal angular velocity of the objects that are not in motion relative to the user, approaches to zero. Moreover, the lock mode is used to fix or stabilize the position and orientation of the user's head, which is obtained through tracking devices, such as the image sensor. The initiation of the lock mode is used to enhance the user's stability during head movements in order to offer an improved comfortable and immersive experience. As a result, the technical effect of controlling the switching of a lock mode during VOR movements, results in a stabilized head pose and gaze direction, which enhances the user's comfort and focus during XR experiences.

Optionally, the modification comprises a low-pass filtering operation applied on one or more gaze directions indicated in the gaze tracking data and one or more head poses indicated in the pose tracking data during the VOR movement (T2). In this regard, the low-pass filtering operation corresponds to a signal processing technique that allows lower-frequency components of a signal to pass through while attenuating higher-frequency components to smoothen and stabilize gaze directions and head poses during the VOR movement. Additionally, the low-pass filtering operation stabilizes the pose-tracking data, enhancing the alignment of the XR environment with the user's head movement. As a result, the user experiences a stable and more realistic XR interaction, making the technology more comfortable and immersive, even in dynamic scenarios, resulting in a more comfortable and visually appealing user experience.

Optionally, the at least one server is further configured to determine whether a smooth pursuit movement is concurrently in progress at the time of detection of the start of the VOR movement (T1) as well as during the VOR movement (T2). Throughout the present disclosure, the term "smooth pursuit movement" refers to a voluntary movement where the eyes remain fixated on a moving object. Most people are unable to initiate pursuit without a moving visual signal. The pursuit of targets moving with velocities greater than 30°/s tends to require catch-up saccades. Smooth pursuit is asymmetric as most humans and primates tend to be better at horizontal than vertical smooth pursuit, as defined by their ability to pursue smoothly without making catch-up saccades. Most humans are also better at downward than upward pursuit. Pursuit is modified by ongoing visual feedback. By recognizing the concurrent smooth pursuit movements, the system is configured to adapt the visual content to minimize motion-related discomfort and enhance the visual experience when it identifies the user's simultaneous smooth pursuit eye movements during a VOR movement. For example, when a user turns his/her head to explore the virtual environment (VOR movement) while smoothly tracking a virtual animal moving within the scene, the system is configured to adjust the XR content dynamically in order to ensure that the animal's motion remains clear and comfortable for the user, providing an overall improved XR experience. Therefore, the technical advantage of determining whether a smooth pursuit movement is concurrently in progress at the time of detection of the start of the VOR movement (T1) as well as during the VOR movement (T2) is to detect and respond to concurrent smooth pursuit eye movements during a VOR movement, ultimately enhancing the XR experience by adapting the content to accommodate the user's head and eye movements in real-time.

Optionally, the modification is applied when the smooth pursuit movement is not concurrently in progress during the VOR movement (T2). The application of the modification when the smooth pursuit movement is not concurrently in progress during the VOR movement (T2) is used to adapt the visual content that is further used to minimize motion-related discomfort and enhance the visual experience specifically when there are no simultaneous smooth pursuit eye movements during the VOR movement. The technical advantage of applying the modification when concurrent smooth pursuit eye movements are not concurrently in progress during the VOR movement (T2) is to provide an optimized and comfortable experience by making real-time adjustments to the XR content and providing visually appealing XR experience during head movements.

Optionally, the at least one server is further configured to distinguish between a smooth pursuit movement and the VOR movement by correlating headset pose changes indicated in the pose tracking data with eye gaze movements indicated in the gaze tracking data of at least one user wearing the at least one display apparatus when in operation.

In this regard, the gaze is held steadily on a location by producing eye movements in the direction opposite that of head movement. For example, when the head moves to the right, the eyes move to the left, meaning the image a user views stays the same even though the position of the head of the user has turned. It is appreciated to note that the slight head movement is present all the time due to which the VOR movement is required for stabilizing the vision. In addition, the smooth pursuit movement can be differentiated from the VOR movement by measuring the headset pose changes in relation to the gaze movement. The technical effect of distinguishing between smooth pursuit movement from the VOR eye movements by correlating headset pose changes with eye gaze movements leads to a more precise, realistic, and engaging XR experience and further optimizes user interaction and alignment with user's behavior, resulting in substantial advantages for the user. The technical effect of distinguishing between a smooth pursuit movement and the VOR movement is to identify whether a user is engaged in smooth pursuit eye tracking (following a moving object with their eyes) or VOR movements (moving their head) based on data from the XR headset accurately, allowing a personalized and improved XR experience based on the user's actions and needs.

The present disclosure also relates to the method as described above. Various embodiments and variants disclosed above, with respect to the aforementioned system, apply mutatis mutandis to the method.

Optionally, the modification comprises a low-pass filtering operation applied on one or more gaze directions indicated in the gaze tracking-data and one or more head poses indicated in the pose tracking-data during the VOR movement (T2).

Optionally, the method further comprises determining whether a smooth pursuit movement is concurrently in progress at the start of the VOR movement (T1) as well as during the VOR movement (T2).

Optionally, the modification is applied when the smooth pursuit movement is not concurrently in progress during the VOR movement (T2).

Optionally, the control of the remote rendering of the extended reality video stream comprises:
tracking an object in motion in a field of view of an image sensor of the at least one display apparatus; and
detecting and differentiating between a movement of the tracked object in motion from a point of view of the image sensor with respect to a stationary perception of the object in motion from a user's eye perspective during the VOR movement (T2).

Optionally, the control of the remote rendering of the extended reality video stream further comprises executing a video see-through (VST) adjustment to balance between deblur and sharpening parameters, based on the differentiation during the VOR movement (T2).

DETAILED DESCRIPTION OF THE DRAWINGS

Referring to FIG. 1, illustrated is a block diagram of an architecture of a system 100 incorporating remote rendering, in accordance with an embodiment of the present disclosure. The system 100 comprises at least one server (for example, depicted as a server 102). The server 102 is communicably coupled to one or more display apparatus (for example, in this case, depicted as display apparatus 104). Optionally, the server 102 is communicably coupled to an image sensor 106 that is configured to capture a field of view (FOV). The server 102 is configured to perform various operations, as described earlier with respect to the aforementioned first aspect.

It may be understood by a person skilled in the art that FIG. 1 includes a simplified architecture of the system 100, for the sake of brevity and clarity, which should not unduly limit the scope of the claims herein. It is to be understood that the specific implementation of the system 100 is provided as an example and is not to be construed as limiting it to specific numbers or types of servers, display apparatuses, and congestion control network devices. The person skilled in the art will recognize many variations, alternatives, and modifications of embodiments of the present disclosure.

Figure 2:
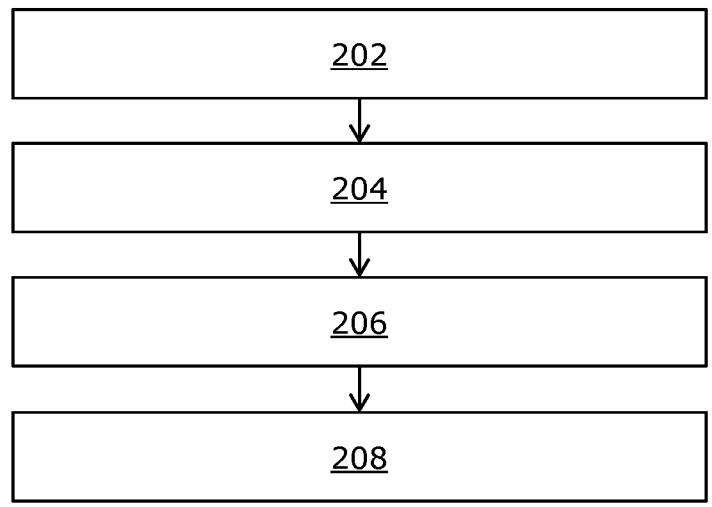
FIG. 2 illustrates steps of a method of remote rendering based on Vestibulo-Ocular Reflex (VOR) movement, in accordance with an embodiment of the present disclosure.

Referring to FIG. 2, illustrated are steps of a method incorporating remote rendering, in accordance with an embodiment of the present disclosure. At step 202, a start of Vestibulo-Ocular Reflex (VOR) movement (T1) is detected based on a gaze tracking-data is detected and a pose tracking-data received from the at least one display apparatus. At step 204, remote rendering of an extended reality video stream at the at least one display apparatus is controlled by modifying a head pose data indicated in the pose tracking-data and a gaze direction data indicated in the gaze tracking-data such that a total retinal angular velocity of a focus target approaches a zero value during the VOR movement (T2). At step 206, an end of the VOR movement (T3) is detected. At step 208, the modification is ended, and video rendering parameters are reverted to pre-set default settings after the end of the VOR movement (T3).

The aforementioned steps are only illustrative and other alternatives can also be provided where one or more steps are added, one or more steps are removed, or one or more steps are provided in a different sequence without departing from the scope of the claims.

Figure 3:
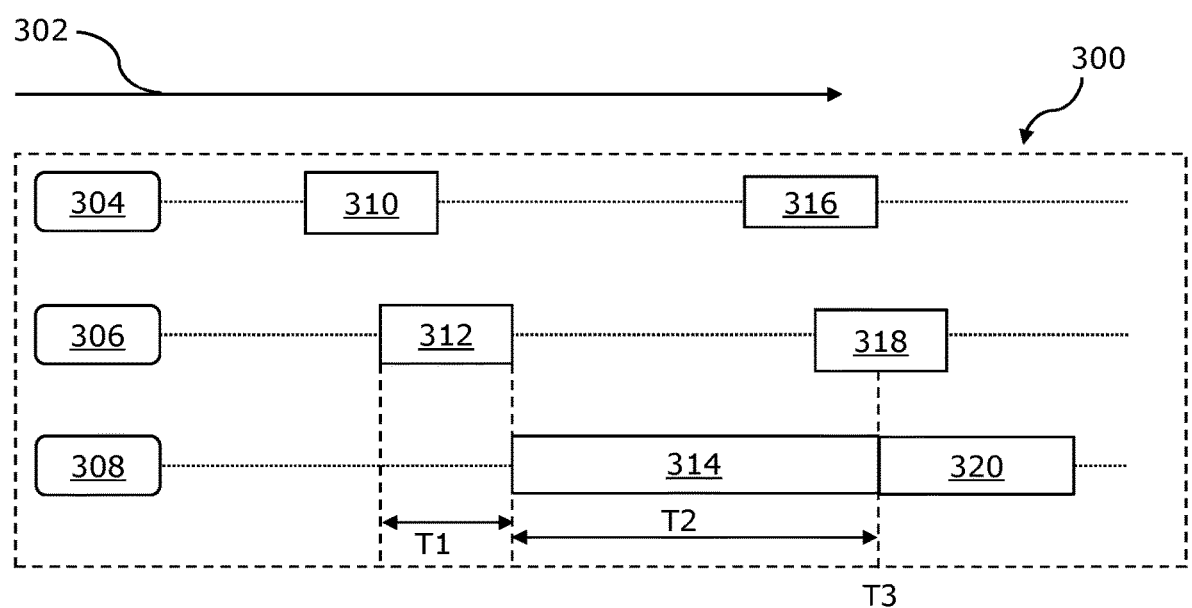
FIG. 3 is an illustration of an exemplary sequence diagram of events in a display apparatus for optimizing image rendering, in accordance with an embodiment of the present disclosure.

Referring to FIG. 3, illustrated is an exemplary sequence diagram of events in the system 100 (of FIG. 1) for optimizing image rendering, in accordance with an embodiment of the present disclosure. In FIG. 3, there is shown an illustration that depicts a sequence 300 of events related to smooth pursuit-aware XR transport. There is shown a time axis 302 that depicts the flow of events with respect to time. There is further shown eyes 304 and certain operations, such as gaze-tracking and pose tracking operations 306 that can be performed by a system (i.e., the system 100 of FIG. 1). In an implementation, the control of remote rendering 308 may be a video stream encoding performed by the server for remote rendering of the video stream at the display apparatus. A gaze-tracking means at the display apparatus tracks the movement of the eyes 304 (e.g., performs the gaze-tracking and pose-tracking 306) and the pose-tracking means at the display apparatus tracks the movement of the head and the neck to detect the head pose of the user.

At 310, the VOR movement of the eyes 304 starts. At 312, the start of the VOR movement (T1) is detected. The server detects the start of the VOR movement (T1) based on a gaze tracking-data and a pose tracking-data received from the at least one display apparatus. In this implementation, the head pose data indicated in the pose tracking-data is collected from the head and the neck movement of the user while the gaze direction data indicated in the gaze tracking-data is collected from the eye movement.

At 314, a low-pass filtering operation is applied on one or more gaze directions indicated in the gaze tracking-data and one or more head poses indicated in the pose tracking-data during the VOR movement (T2). Furthermore, the at least one server is further configured to control switching of a lock mode at the at least one display apparatus to lock a head pose indicated in the pose tracking-data and the gaze direction indicated in the gaze tracking-data during the VOR movement (T2).

At 316, the VOR movement of the eyes 304 ends. At 318, the end of the VOR movement (T3) is detected. The server detects the end of the VOR movement (T3) based on the movement information received from the display apparatus. In this case, the eye movement information comprises the gaze-tracking data and the pose-tracking data that indicates the end of the VOR movement (T3).

At 320, the video rendering parameters are reverted to pre-set default settings after the end of the VOR movement (T3). As a result, the VOR-aware XR rendering is achieved, thereby improving image quality, and reducing latency in the display apparatus (e.g., an XR headset).

FIG. 3 is merely an example, which should not unduly limit the scope of the claims herein. A person skilled in the art will recognize many variations, alternatives, and modifications of embodiments of the present disclosure.

The invention claimed is:

1. A system comprising at least one server that is communicably coupled to at least one display apparatus, wherein the at least one server is configured to:
   detect a start of a Vestibulo-Ocular Reflex (VOR) movement based on a gaze tracking-data and a pose tracking-data received from the at least one display apparatus;
   control remote rendering of an extended reality video stream at the at least one display apparatus by modifying a head pose data indicated in the pose tracking-data and a gaze direction data indicated in the gaze tracking-data such that a total retinal angular velocity of a focus target approaches a zero value during a VOR movement;
   detect an end of the VOR movement; and
   stop the modification and revert video rendering parameters to pre-set default settings after the end of the VOR movement.

2. The system of claim 1, wherein the modification comprises a low-pass filtering operation applied on one or more gaze directions indicated in the gaze tracking-data and one or more head poses indicated in the pose tracking-data during the VOR movement.

3. The system of claim 1, wherein the at least one server is further configured to determine whether a smooth pursuit movement is concurrently in progress at the time of detection of the start of the VOR movement as well as during the VOR movement.

4. The system of claim 3, wherein the modification is applied when the smooth pursuit movement is not concurrently in progress during the VOR movement.

5. The system of claim 1, wherein the control of the remote rendering of the extended reality video stream comprises:
   tracking an object in motion in a field of view of an image sensor of the at least one display apparatus; and
   detecting and differentiating between a movement of the tracked object in motion from a point of view of the image sensor with respect to a stationary perception of the object in motion from a user's eye perspective during the VOR movement.

6. The system of claim 5, wherein the control of the remote rendering of the extended reality video stream further comprises executing a video see-through (VST) adjustment to balance between deblur and sharpening parameters, based on the differentiation during the VOR movement.

7. The system of claim 1, wherein the at least one server is further configured to distinguish between a smooth pursuit movement and the VOR movement by correlating headset pose changes indicated in the pose tracking-data with eye gaze movements indicated in the gaze tracking-data of at least one user wearing the at least one display apparatus when in operation.

8. The system of claim 1, wherein the at least one server is further configured to utilize a combination of the gaze-tracking data and the pose-tracking data as an additional datapoint during the VOR movement to refine tracking of at least one or both of the head pose and the gaze-direction.

9. The system of claim 1, wherein the at least one server is further configured to control switching of a lock mode at the at least one display apparatus to lock a head pose indicated in the pose tracking-data and the gaze direction indicated in the gaze tracking-data during the VOR movement.

10. A method of remote rendering implemented by at least one server, the method comprising:
    detecting a start of a Vestibulo-Ocular Reflex (VOR) movement based on a gaze tracking-data and a pose tracking-data received from the at least one display apparatus;
    controlling remote rendering of an extended reality video stream at the at least one display apparatus by modifying a head pose data indicated in the pose tracking-data and a gaze direction data indicated in the gaze tracking-data such that a total retinal angular velocity of a focus target approaches a zero value during the VOR movement;
    detecting an end of the VOR movement; and
    ending the modification and reverting video rendering parameters to pre-set default settings after the end of the VOR movement.

11. The method of claim 10, wherein the modification comprises a low-pass filtering operation applied on one or more gaze directions indicated in the gaze tracking-data and one or more head poses indicated in the pose tracking-data during the VOR movement.

12. The method of claim 10, further comprising determining whether a smooth pursuit movement is concurrently in progress at the start of the VOR movement as well as during the VOR movement.

13. The method of claim 12, wherein the modification is applied when the smooth pursuit movement is not concurrently in progress during the VOR movement.

14. The method of claim 10, wherein the control of the remote rendering of the extended reality video stream comprises:
    tracking an object in motion in a field of view of an image sensor of the at least one display apparatus; and
    detecting and differentiating between a movement of the tracked object in motion from a point of view of the image sensor with respect to a stationary perception of the object in motion from a user's eye perspective during the VOR movement.

15. The method of claim 14, wherein the control of the remote rendering of the extended reality video stream further comprises executing a video see-through (VST) adjustment to balance between deblur and sharpening parameters, based on the differentiation during the VOR movement.

* * * * *